United States Patent
Kawamura et al.

(10) Patent No.: US 8,107,709 B2
(45) Date of Patent: Jan. 31, 2012

(54) APPARATUS AND METHOD FOR PROCESSING RADIATION IMAGE

(75) Inventors: Takahiro Kawamura, Minami-ashigara (JP); Sadato Akahori, Odawara (JP); Kazuharu Ueta, Tokyo (JP); Yasunori Ohta, Yokohama (JP); Atsushi Fukuda, Koganei (JP)

(73) Assignee: Fujifilm Corporation, Tokyo (JP)

( * ) Notice: Subject to any disclaimer, the term of this patent is extended or adjusted under 35 U.S.C. 154(b) by 804 days.

(21) Appl. No.: 12/212,706

(22) Filed: Sep. 18, 2008

(65) Prior Publication Data

US 2009/0080755 A1   Mar. 26, 2009

(30) Foreign Application Priority Data

Sep. 26, 2007   (JP) .................... 2007-248330

(51) Int. Cl.
*G06K 9/00* (2006.01)
(52) U.S. Cl. .............. 382/132; 378/62; 378/98.11
(58) Field of Classification Search .......... 382/128, 382/130–132; 378/62, 98.11, 98.12
See application file for complete search history.

(56) References Cited

U.S. PATENT DOCUMENTS

| 6,501,819 | B2 | 12/2002 | Unger et al. |
| 6,643,536 | B2 | 11/2003 | Nicolas et al. |
| 6,661,873 | B2 | 12/2003 | Jabri et al. |
| 6,917,697 | B2 | 7/2005 | Avinash et al. |

FOREIGN PATENT DOCUMENTS

| JP | 2002-325756 A | 11/2002 |
| JP | 2002-330954 A | 11/2002 |
| JP | 2003-037778 A | 2/2003 |
| JP | 2003-244542 A | 8/2003 |

*Primary Examiner* — Courtney Thomas
(74) *Attorney, Agent, or Firm* — Sughrue Mion, PLLC

(57) ABSTRACT

The present invention relates to a radiation image processing apparatus and a processing method. A processing condition selector selects from a processing condition memory a processing condition for extraction or removal of a specific object in radiation image information. The processing condition includes two different image capturing conditions which are provided to a radiation source controller. The radiation source controller controls a radiation source with each image capturing condition to apply radiation to a subject and a solid-state radiation detector stores radiation image information of the subject. An image processor performs a weighted subtraction using stored radiation image information in accordance with the processing condition to achieve extraction or removal of the specific object. The resultant radiation image information is displayed on a display unit.

9 Claims, 4 Drawing Sheets

FIG. 2

| PROCESSING CONDITION | SPECIFIC OBJECT | IMAGE CAPTURING SITE | FIRST IMAGE CAPTURING CONDITION ($S_1$) | SECOND IMAGE CAPTURING CONDITION ($S_2$) | WEIGHTING COEFFICIENT ($\alpha$) |
|---|---|---|---|---|---|
| A | SOFT TISSUE | CHEST | 60kVp/5mAs | 120kVp/2mAs | −0.5 |
| B | BONE | CHEST | 60kVp/5mAs | 120kVp/2mAs | −0.9 |
| C | PLASTER CAST | CHEST | 50kVp/20mAs | 120kVp/6mAs | −0.45 |
| D | CATHETER | CHEST (CHILD) | 50kVp/10mAs | 120kVp/3mAs | −0.6 |

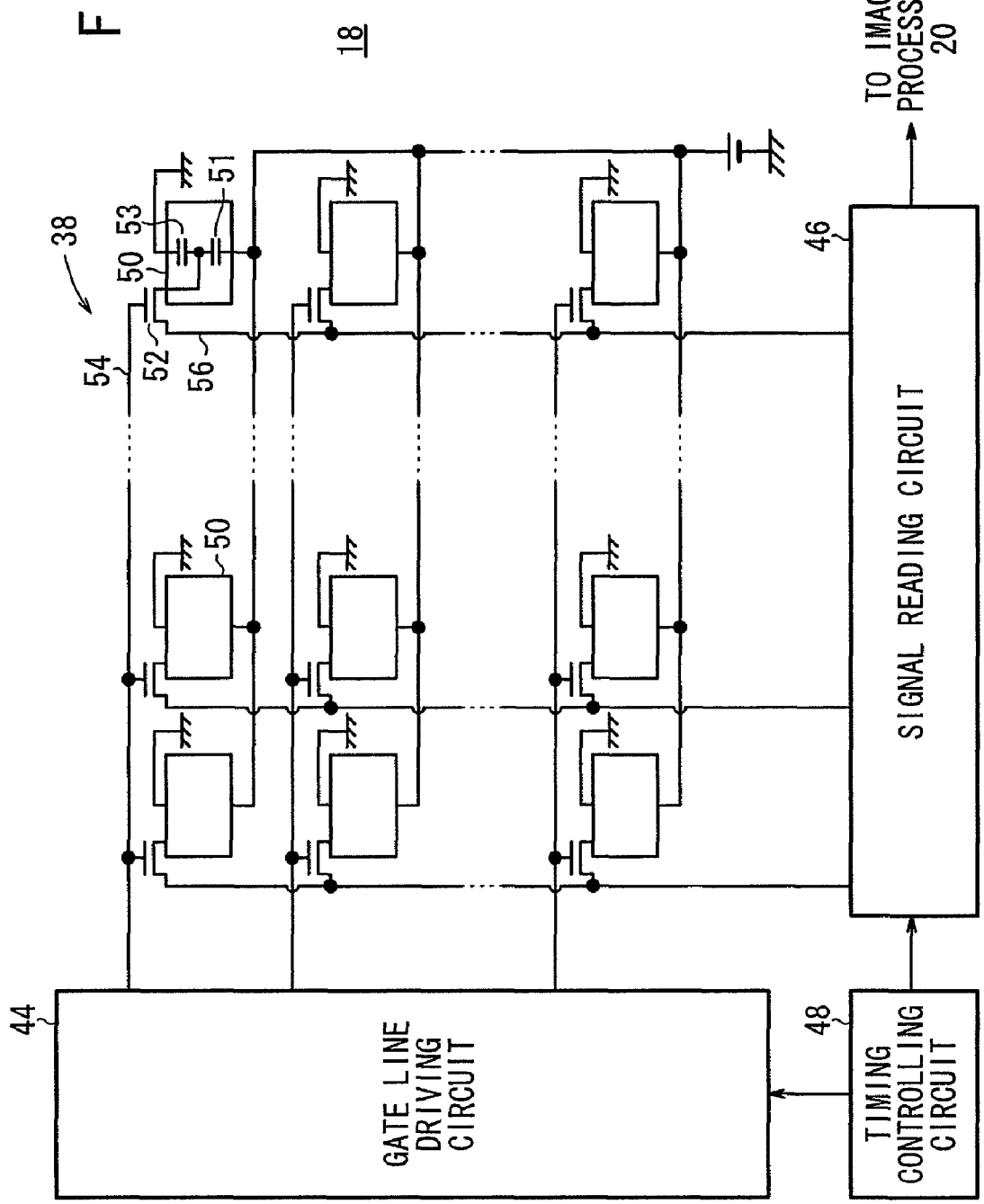

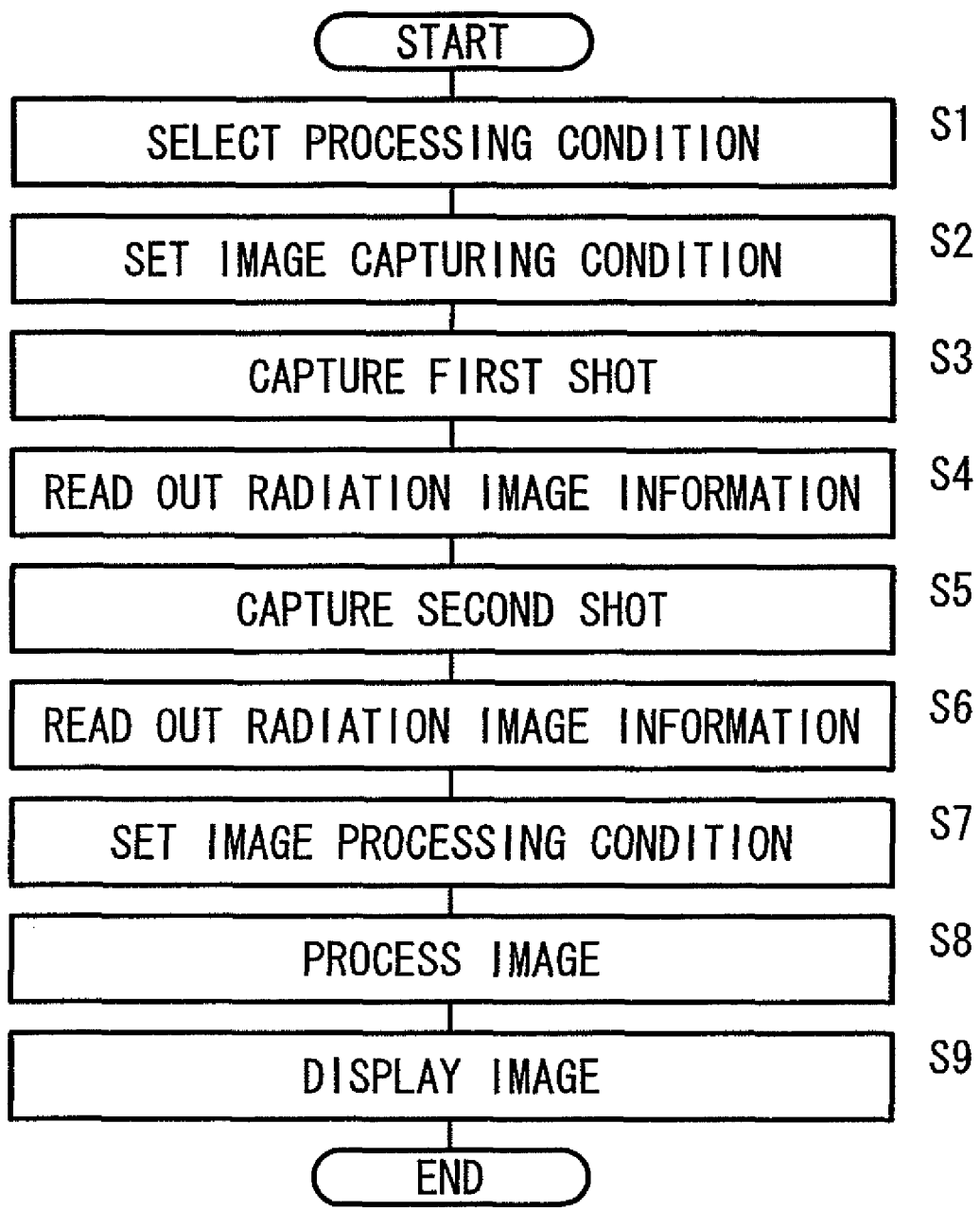

APPARATUS AND METHOD FOR PROCESSING RADIATION IMAGE

BACKGROUND OF THE INVENTION

1. Field of the Invention

The present invention relates to a radiation image processing apparatus and a processing method for extraction or removal of a specific object in a radiation image using a plurality of pieces of radiation image information acquired by applying radiation of different energies to a subject.

2. Description of the Related Art

In the medical field, for example, extensive use is made of radiation image processing apparatus which expose a subject (patient) to radiation emitted from a radiation source, guide the radiation that has passed through the subject to a radiation converting panel for converting radiation into radiation image information, and then perform predetermined image processing on the radiation image information. Processed radiation image information is displayed on a display unit and can be used for diagnosis etc.

One example of the radiation converting panel is a solid-state detector that converts radiation into charge information and stores the charge information so that it can be read out as an electric signal. Another example of the radiation converting panel is a stimulable phosphor panel. The stimulable phosphor panel stores radiation energy in a phosphor and emits stimulated light of an intensity corresponding to the stored energy when irradiated with stimulating light such as a laser beam.

One practical application of the radiation image apparatus is the extraction of a region of interest in the subject, e.g., soft tissue such as the heart and lungs located under ribs, from the radiation image information. The extraction of the region of interest is achieved based on a difference in absorption characteristics between bone such as the ribs and soft tissue such as the heart. Radiation of different energies is applied to the subject using two different image capturing conditions to acquire two pieces of radiation image information. The extraction of the bone or soft tissue of interest is achieved by computing the difference between the two pieces of radiation image information with predetermined weighting coefficients.

Since different internal structures of the subject have different radiation absorption characteristics, it is necessary to process the image in accordance with these characteristics to acquire a proper image of the region of interest.

Japanese Laid-Open Patent Publications Nos. 2003-037778 and 2003-244542 disclose image processing method in which the extraction of bone or soft tissue is achieved using a predetermined relation between radiation source tube voltages, which determine the radiation dose to the subject, and weighting coefficients used for computing a difference between the pieces of radiation image information. The image processing method disclosed in Japanese Laid-Open Patent Publication No. 2002-330954, acquires a first piece of radiation image information by applying radiation to a subject in accordance with a predetermined image capturing condition. Then, the image capturing condition is modified based on analysis of the first piece of radiation image information, and used for acquisition of a second piece of radiation image information. Finally, an image of a region of interest is produced from the first and second pieces of radiation image information.

The methods disclosed in Japanese Laid-Open Patent Publications Nos. 2003-037778 and 2003-244542, however, require highly experienced operators for the determination of a suitable tube voltage and weighting coefficient for a region of interest. Further, the above-mentioned Publications are only concerned with the tissue of a subject, and no consideration is given to methods for extraction or removal of a foreign body within a subject. The method disclosed in Japanese Laid-Open Patent Publication No. 2002-330954, which determines the image capturing condition for the second piece of radiation image information based on the first piece of radiation image information, may fail to obtain proper image information when the subject moves before the acquisition of the second piece of radiation image information.

SUMMARY OF THE INVENTION

It is a general object of the invention to provide a radiation image processing apparatus and processing method for easily and reliably extracting and removing a desired specific object in a subject from radiation image information.

It is a main object of the invention to provide a radiation image processing apparatus and processing method that allow acquisition of radiation image information of a desired specific object without being highly experienced in image processing.

It is another object of the invention to provide a radiation image processing apparatus and processing method that allow acquisition of radiation image information of a desired specific object in a subject quickly and with high accuracy.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 2 illustrates a processing condition table stored in a processing condition memory of the radiation image processing apparatus of FIG. 1;

FIG. 3 is a block diagram illustrating a circuit configuration of a radiation detector according to an embodiment of the invention; and FIG. 4 is a flowchart illustrating the operation of the radiation image processing apparatus of FIG. 1.

DESCRIPTION OF THE PREFERRED EMBODIMENTS

Figure 1:
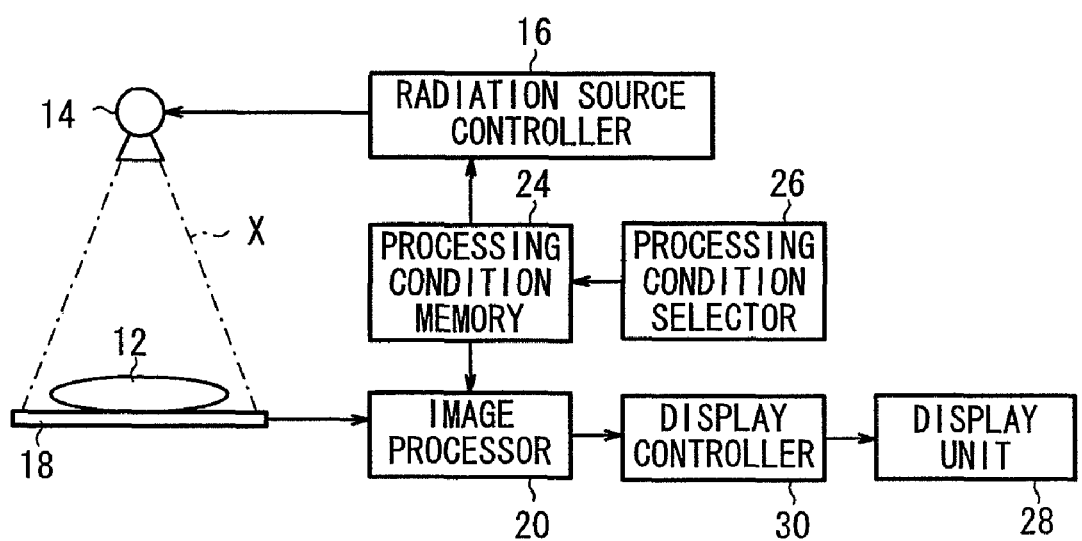
FIG. 1 is a block diagram illustrating a configuration of a radiation image processing apparatus according to an embodiment of the invention.

FIG. 1 is a block diagram illustrating a configuration of a radiation image processing apparatus 10 according to an embodiment of the present invention.

The radiation image processing apparatus 10 includes a radiation source 14 for applying radiation X to a subject 12, a radiation source controller 16 for controlling the radiation source 14 in accordance with predetermined image capturing conditions such as a tube voltage, a tube current, and irradiation time, and a solid-state radiation detector 18 (radiation converting panel) for converting the radiation X that has passed through the subject 12 into charge information that serves as radiation image information. The radiation image processing apparatus 10 further includes an image processor 20 for processing the radiation image information detected by the solid-state radiation detector 18, a processing condition memory 24 for storing processing conditions including the above-mentioned image capturing conditions in the form of a processing condition table shown in FIG. 2, and a processing condition selector 26 for retrieving from the processing condition memory 24 a processing condition required for producing desired radiation image information. The radiation image processing apparatus 10 also includes a display unit 28 for displaying the radiation image information processed by the image processor 20, and a display controller 30 for controlling the display unit 28.

The image processor 20 performs extraction or removal of a specific object within the subject 12 from a radiation image by carrying out weighted subtraction using a plurality of pieces of radiation image information obtained at different radiation energies. The weighted subtraction is computed as $$S = \alpha \cdot S_1 + S_2$$

where S is a resultant piece of radiation image information, $S_1$ and $S_2$ are pieces of radiation image information obtained with first and second image capturing conditions, respectively, and $\alpha$ is a weighting coefficient.

In order to obtain a resultant image having suitable contrast and brightness after the extraction or removal of the specific object, the weighted subtraction may alternatively be computed as $$S = K_1 \cdot S_1 + K_2 \cdot S_2 + K_3$$

where $K_1$, $K_2$ and $K_3$ are coefficients determined by the weight coefficient for extraction or removal of the specific object and the gradation characteristics of the first and second pieces of radiation image information $S_1$ and $S_2$.

FIG. 2 shows the processing condition table 22 stored in the processing condition memory 24 of FIG. 1. In the present embodiment, the processing condition table 22 includes a first image capturing condition ($S_1$), a second image capturing condition ($S_2$), and a weighting coefficient $\alpha$, corresponding to a specific object and an image capturing site. The first and second image capturing conditions ($S_1$ and $S_2$) and the weighting coefficient $\alpha$ are determined so as to minimize exposure dose of the subject 12. Each of the first and second image capturing conditions ($S_1$ and $S_2$) includes a tube voltage and a tube current to be set to the radiation source 14. Processing conditions A though D represent the condition required for extracting soft tissue in a chest, the condition for extracting bone in a chest, the condition for removing a plaster cast around a knee, and the condition for removing a catheter inserted into a child's chest, respectively. Note that the processing condition table 22 may also include other processing conditions such as a condition for extraction or removal of an internally-located foreign body, which may be made of glass, plastic, metal, or the like. Such a condition may be determined based on the radiation absorption characteristics of the material of the foreign body. Note that the first and second image capturing conditions ($S_1$ and $S_2$) may remain constant for all processing conditions, while the weighting coefficient $\alpha$ varies with the specific object and the image capturing site. On the other hand, a fixed weighting coefficient $\alpha$ may be used for all processing conditions, while varying the first and second image capturing conditions ($S_1$ and $S_2$) with the specific object and the image capturing site.

FIG. 3 is a block diagram illustrating a circuit configuration of the solid-state radiation detector 18. The solid-state radiation detector 18 includes a sensor substrate 38, a gate line driving circuit 44, a signal reading circuit 46, and a timing control circuit 48 that controls the gate line driving circuit 44 and the signal reading circuit 46.

The sensor substrate 38 includes a two-dimensional array of Thin Film Transistors (TFTs) 52 and a photoelectric conversion layer 51 disposed over the TFTs 52. The photoelectric conversion layer 51 is made of a material such as amorphous selenium (a-Se), which generates charge on sensing radiation X. The sensor substrate 38 stores the charge generated by the a-Se layer into storage capacitors 53. Then, the TFTs 52 in each row of the two-dimensional array are sequentially switched on to allow the charge of the storage capacitors 53 to be read out as image signals. FIG. 3 only shows the connection between one TFT 52 and one pixel 50 which is made up of one storage capacitor 53 and a corresponding part of the photoelectric conversion layer 51. The details of other pixels 50 are omitted for clarity. Note that the amorphous selenium shows performance degradation at high temperatures because of an inherent structural change, and the amorphous selenium must therefore be used within a predetermined temperature range. The TFT 52 of each pixel 50 is connected to a gate line 54 extending in the row direction of the TFT array and a signal line 56 extending in the column direction of the TFT array. Each gate line 54 is connected to the gate line driving circuit 44, and each signal line 56 is connected to the signal reading circuit 46.

The radiation image processing apparatus 10 according to the embodiment of the present invention is essentially configured as described above. Now, the operation of the radiation image processing apparatus 10 will be described with reference to the flowchart shown in FIG. 4.

First, an operator selects one of the processing conditions stored in the processing condition memory 24 using the processing condition selector 26 (step S1). If, for example, radiation image information of soft tissue of the chest of the subject 12 is desired, the processing condition A is selected from the processing condition table 22 of the processing condition memory 24.

Next, the first and second image capturing conditions ($S_1$ and $S_2$) of the selected processing condition are provided to the radiation source controller 16 (step S2).

A first shot is then captured by applying radiation X to the subject 12 with the radiation source controller 16 controlling the tube voltage and the tube current of the radiation source 14 in accordance with the first image capturing condition ($S_1$) (step S3).

The radiation X that has passed through the subject 12 is converted into an electric signal by the photoelectric conversion layer 51 of the pixels 50 which make up the sensor substrate 38 of the solid-state radiation detector 18. The electric signal is then stored into the storage capacitor 53 as charge. Then, the timing control circuit 48 supplies timing control signals to the gate line driving circuit 44 and the signal reading circuit 46 to allow readout from each storage capacitor 53 of the charge information representing the first shot radiation image information $S_1$ of the subject 12.

More specifically, the gate line driving circuit 44 selects one of the gate lines 54 in accordance with the timing control signal provided by the timing control circuit 48 and supplies a driving signal to the base terminal of each TFT 52 connected to the selected gate line 54. Meanwhile, the signal reading circuit 46 selects the signal lines 56 connected to the charge detecting circuits 57 one after another in the row direction of the TFT array in accordance with the timing control signals provided from the timing control circuit 48. As a result, the storage capacitor 53 of the pixel 50 corresponding to the selected gate line 54 and signal line 56 discharges the charge information associated with the piece of radiation image information $S_1$, and the image processor 20 receives this charge information as an image signal. After the image signal from each of the pixels 50 arranged in the selected row has been read out, the gate line driving circuit 44 selects the next gate line 54 in the column direction and supplies the driving signal to the selected gate line 54. The signal reading circuit 46 then reads out image signals from the TFTs 52 connected to the selected gate line 54 in the same manner. By repeating the operation described above, the two-dimensional piece of radiation image information $S_1$ stored in the sensor substrate 38 is read out and provided to the image processor 20 (step S4).

Next, a second shot is captured by applying radiation X to the subject 12 with the radiation source controller 16 controlling the tube voltage and tube current of the radiation source 14 in accordance with the second image capturing condition ($S_2$) (step S5). It should be noted that the second shot is performed immediately after the first shot by the use of the predetermined second image capturing condition ($S_2$). Therefore, motion artifacts caused by the movement of the subject 12 between the first and second shots do not occur.

The second shot radiation image information $S_2$ detected by the solid-state radiation detector 18 is read out in the same manner as the first shot radiation image information $S_1$ and provided to the image processor 20 (step S6). If the subject 12 has moved between the first and second shots, the image processor 20 processes the supplied information to correct the positional relation of the images associated with the pieces of radiation image information $S_1$ and $S_2$ before performing further processing.

Next, the weighting coefficient α specified in the processing condition selected by the processing condition selector 26 from the processing condition memory 24 is provided to the image processor 20 (step S7).

The image processor 20 then calculates in step S8 a piece of radiation image information S from the pieces of radiation image information $S_1$ and $S_2$ supplied by the solid-state radiation detector 18 and the weighting coefficient α selected from the processing condition memory 24 using $$S = \alpha \cdot S_1 + S_2.$$

The resultant piece of radiation image information S is displayed on the display unit 28 by the display controller 30 (step S9). The display unit 28 shows a radiation image in which the specific object selected by the processing condition selector 26 is extracted, or a radiation image in which the specific object is removed. For example, it should be noted that the image processor 20 may also be provided with a processing condition for extraction of a foreign object, so that radiation image information can be computed and displayed to facilitate identification of the foreign object within the body of the subject 12.

It should be noted that the present invention is not limited to the embodiment described above and various variations and modifications may be made without departing from the scope of the invention.

For example, instead of the solid-state radiation detector 18 that converts applied radiation X directly into charge information, a radiation detector may be employed that converts radiation X into visible light by means of a scintillator, and then converts the visible light into charge information. Alternatively, an optical readout radiation detector may be utilized. The optical readout radiation detector may store radiation X as a latent image and allow the latent image to be read out as charge information when scanned with reading light. Another possibility is to employ a stimulable phosphor panel, which stores radiation energy in a phosphor and emits stimulated light of an intensity corresponding to the stored energy when irradiated with stimulating light such as a laser beam.

What is claimed is:

1. A radiation image processing apparatus that performs extraction or removal of a specific object in a radiation image using a plurality of pieces of radiation image information, each obtained by applying radiation to a subject at different radiation energies, the apparatus comprising:
    a radiation source for applying the radiation to the subject;
    a radiation source controller for controlling the radiation source in accordance with different image capturing conditions;
    a radiation converting panel for receiving and converting the radiation that has passed through the subject into radiation image information;
    a processing condition memory for storing processing conditions, the processing conditions including the image capturing conditions for extraction and removal of the specific object;
    a processing condition selector for selecting from the processing conditions in the processing condition memory a processing condition corresponding to the target; and
    an image processor for processing, in accordance with the selected processing condition, the plurality of pieces of radiation image information obtained from the radiation converting panel with the different image capturing conditions.

2. The apparatus according to claim 1, wherein the image capturing condition includes a tube voltage and a tube current for the radiation source, the tube voltage and tube current depending on a type of the specific object.

3. The apparatus according to claim 1, wherein the processing condition includes a weighting coefficient for a weighted subtraction using the plurality of pieces of radiation image information obtained from the radiation converting panel.

4. A radiation image processing method that performs extraction or removal of a specific object in radiation image information using a plurality of pieces of radiation image information, each obtained by applying radiation to a subject at different radiation energies, the method comprising the steps of:
    setting a processing condition including different image capturing conditions in order to perform extraction or removal of the specific object;
    controlling a radiation source in accordance with the different image capturing conditions, and applying the radiation to a radiation converting panel through the subject; and
    processing, in accordance with the processing condition, the plurality of pieces of radiation image information obtained from the radiation converting panel with the different image capturing conditions.

5. The method according to claim 4, wherein the image processing of the plurality of pieces of radiation image information includes performing a weighted subtraction using the plurality of pieces of radiation image information obtained from the radiation converting panel, and the processing condition includes a weighting coefficient for performing the weighted subtraction.

6. The method according to claim 5, wherein the weighted subtraction is computed using $$S = \alpha \cdot S_1 + S_2$$

where S is a piece of resultant radiation image information, $S_1$ is a piece of the radiation image information obtained with a first one of the image capturing conditions, $S_2$ is a piece of the radiation image information obtained with a second one of the image capturing conditions, and α is the weighting coefficient.

7. The method according to claim 6, wherein the first and second image capturing conditions remain fixed, and the weighting coefficient α varies with the specific object and the image capturing site.

8. The method according to claim 6, wherein the weighting coefficient α remains fixed, and the first and second image capturing conditions vary with the specific object and the image capturing site.

9. The method according to claim 5, wherein the weighted subtraction is computed using $$S = K_1 \cdot S_1 + K_2 \cdot S_2 + K_3$$

where S is a resultant piece of radiation image information, $S_1$ is the piece radiation image information obtained with a first one of the image capturing conditions, $S_2$ is the piece of radiation image information obtained with a second one of the image capturing conditions, and $K_1$, $K_2$ and $K_3$ are weighting coefficients for adjusting contrast and brightness.

* * * * *